(12) United States Patent
Saxena et al.

(10) Patent No.: US 10,391,179 B2
(45) Date of Patent: *Aug. 27, 2019

(54) ORGANOMODIFIED CARBOSILOXANE MONOMERS CONTAINING COMPOSITIONS AND USES THEREOF

(75) Inventors: Anubhav Saxena, Bangalore (IN); Umpathy Senthilkumar, Bangalore (IN); Kenrick M. Lewis, Flushing, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/052,288

(22) Filed: Mar. 21, 2011

(65) Prior Publication Data

US 2012/0244088 A1   Sep. 27, 2012

(51) Int. Cl.
| | |
|---|---|
| *A61K 8/58* | (2006.01) |
| *A61K 47/34* | (2017.01) |
| *A61Q 19/00* | (2006.01) |
| *A61K 8/81* | (2006.01) |
| *A61K 8/895* | (2006.01) |
| *C07F 7/08* | (2006.01) |

(52) U.S. Cl.
CPC .............. *A61K 47/34* (2013.01); *A61K 8/585* (2013.01); *A61K 8/8152* (2013.01); *A61K 8/895* (2013.01); *A61Q 19/00* (2013.01); *C07F 7/0838* (2013.01); *A61K 2800/10* (2013.01)

(58) Field of Classification Search
CPC .................................................... A61K 8/585
See application file for complete search history.

(56) References Cited

U.S. PATENT DOCUMENTS

| | | | |
|---|---|---|---|
| 4,433,125 A * | 2/1984 | Ichinohe et al. ............ | 526/279 |
| 5,347,028 A | 9/1994 | Buese et al. | |
| 6,391,999 B1 | 5/2002 | Crivello | |
| 2004/0040554 A1 | 3/2004 | Matsuoka et al. | |
| 2011/0009519 A1 | 1/2011 | Awasthi et al. | |
| 2011/0009658 A1 | 1/2011 | Awasthi et al. | |

FOREIGN PATENT DOCUMENTS

| | | |
|---|---|---|
| EP | 0367381 A2 | 5/1990 |
| EP | 2258412 A1 | 12/2010 |
| GB | 2137635 A | 10/1984 |
| WO | 2009085298 A2 | 7/2009 |
| WO | 2009085299 A2 | 7/2009 |
| WO | 2010038242 A2 | 4/2010 |
| WO | WO2010/038242 A2 * | 4/2010 |

OTHER PUBLICATIONS

Efimov YT, Tandura TA, Kopylov VM, Andronsenko SI and Shkol'nik MI. Synthesis of Organosilicon derivatives of acrylic acids. Journal of General Chemistry USSR, 1991; 61(10): 2083-2091, cited in the IDS.*
(J. G. Cannon, Chapter Nineteen in Burger's Medicinal Chemistry and Drug Discovery, Fifth Edition, vol. I: Principles and Practice, Wiley-Interscience 1995, pp. 783-802).*
Greber, G. et al., "Über oligomere siliciumverbindungen mit funktionellen gruppen. 7. Mitt.: Über die herstellung und polymerisation von vinyl-und allylpolysilmethylenen", Makromolekulare Chemie, vol. 52, Jan. 1, 1962, pp. 184-198.
Omotowa, B. A. et al., "Preparation and Characterization of Nonpolar Fluorinated Carbosilane Dendrimers by APcI Mass Spectrometry and Small Angle X-ray Scattering," J. Am. Chem. Soc., vol. 121, 1999, pp. 11130-11138.
Ishikawa, M. et al., "Photochemically Generated Silicon-Carbon Double-Bonded Intermediates", J. Organometal. Chem., vol. 149, 1978, pp. 37-48.
Efimov, Yu T. et al., "Synthesis of Organosilicon Derivatives of Acrylic Acids," Journal of General Chemistry of the USSR, vol. 61, No. 10 part 2, Oct. 1, 1991, pp. 2083-2091.
Hill and Fatt (American Journal of Optometry, vol. 47, p. 50, 1970).
Bok Y. Lee "The Wound Management Manual", McGraw-Hill, New York 2005, p. 44.

* cited by examiner

*Primary Examiner* — Marcos L Sznaidman
*Assistant Examiner* — Rayna Rodriguez
(74) *Attorney, Agent, or Firm* — Joseph S. Ostroff

(57) ABSTRACT

There is provided novel mono-acrylate functionalized siloxane monomer containing carbosiloxane linkage for improved hydrolysis resistance. This invention also provides copolymers produced using these monomers and their use in various applications.

17 Claims, No Drawings

ORGANOMODIFIED CARBOSILOXANE MONOMERS CONTAINING COMPOSITIONS AND USES THEREOF

FIELD OF THE INVENTION

The present invention relates to a composition comprising novel mono-acrylate functionalized organo modified carbosiloxane monomer that exhibits improved hydrolytic stability under acidic, basic and neutral pH conditions in comparison to the corresponding conventional siloxane monomer. More particularly the present invention relates to improved compositions comprising hydrolytic stability at the pH of 6.5, 7.0 and 7.5.

BACKGROUND OF THE INVENTION

Any publications or references discussed herein are presented to describe the background of the invention and to provide additional detail regarding its practice. Nothing herein is to be construed as an admission that the inventors are not entitled to antedate such disclosure by virtue of prior invention.

Siloxane based hydrogels are used for variety of applications in the area of health care, personal care, agriculture, coatings, home care etc, because of their water absorbing and high oxygen permeable nature. However these silicone hydrogels show poor hydrolytic stability under acidic or basic pH conditions. This effect is predominant when the siloxane chain length is too small. Especially, the trisiloxane-based compounds are well known to undergo rapid hydrolytic cleavage under acidic or basic pH conditions. The instant invention discloses siloxane compositions that are hydrolytically more stable and can be used to form hydrolytically stable silicone hydrogel copolymer that can be potentially used for various applications, including those cited above.

Carbomer is a generic name for synthetic high molecular weight polymers of acrylic acid used as thickening, dispersing, suspending and emulsifying agents in pharmaceuticals and cosmetics. They may be homopolymers of acrylic acid, as well as copolymers with methacrylic acid and other acrylates.

SUMMARY OF THE INVENTION

An object of the present invention is to provide a mono-acrylate functional organo-modified carbosiloxane composition comprising a silicone monomer having the following general formulae (I):

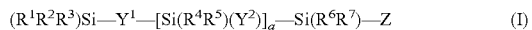

wherein a is 0 to about 100; $Y^1$ is a substituted or unsubstituted divalent alkyl linking group of 1 to about 10 carbon atoms; $Y^2$ is a substituted or unsubstituted divalent alkyl linking group of 1 to about 10 carbon atoms or a hetero atom such as nitrogen, oxygen or sulfur; $R^1$, $R^2$, $R^3$, $R^4$, $R^5$, $R^6$, and $R^7$ are independently selected from the group consisting of monovalent aliphatic, cycloaliphatic or aromatic hydrocarbon groups of 1 to about 10 carbons and halogenated hydrocarbon groups of 1 to about 10 carbons, —$Y^2$—Si($R^8R^9R^{10}$) and A, wherein $R^8R^9R^{10}$ are independently selected from the group consisting of monovalent aliphatic, cycloaliphatic and aromatic hydrocarbon groups of 1 to about 10 carbons; A is a monovalent hydrophilic or hydrophobic moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; Z has the following general formula (II)

wherein $R^{11}$ is a linear or branched, divalent alkyl linking group having 0 to about 20 carbon atoms; B is a divalent hydrophilic or hydrophobic moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; and X is a polymerizable group having the following general formula (III)

wherein $R^{12}$, $R^{13}$, and $R^{14}$ is hydrogen or a substituted or unsubstituted saturated monovalent hydrocarbon group of 1 to about 20 carbons.

Another object of the present invention is to provide a silicone composition comprising homo and copolymers derived from the monomers described herein.

Another object of the present invention is to provide a carbomer-containing composition exhibiting a high level of dispersion of its carbomer component, useful in the preparation of various personal care products, cosmetics and the like. The inventive composition and formulations made there from are efficiently and effectively realized employing conventional equipment and standard manufacturing practices.

Another embodiment of the present invention is directed to a process for producing the described silicone monomers comprising chemically reacting a silicone-containing compound having the general formula shown below

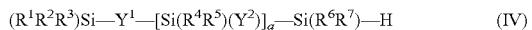

wherein a is 0 to 100; $Y^1$ is a substituted or unsubstituted divalent alkyl linking group of 1 to 10 carbon atoms, and $Y^2$ can be the same as $Y^1$ or a hetero atom such as nitrogen, oxygen or sulfur. $R^1$ to $R^7$ is independently selected from the group consisting of monovalent aliphatic, cycloaliphatic or aromatic hydrocarbon groups of 1 to about 10 carbons and halogenated hydrocarbon groups of 1 to about 10 carbons. Also, $R^1$-$R^7$ can be —$Y^2$—Si($R^8R^9R^{10}$) and A, wherein $R^8$ to $R^{10}$ is independently selected from the group consisting of monovalent aliphatic, cycloaliphatic or aromatic hydrocarbon groups of 1 to about 10 carbons and halogenated hydrocarbon groups of 1 to about 10 carbons. A can be a monovalent hydrophilic or hydrophobic moiety selected from the group consisting of, substituted or unsubstituted, saturated and unsaturated aliphatic, cycloaliphatic or aromatic hydrocarbons and optionally contains hetero atoms. Once produced it is reacted with terminally unsaturated group having the general formula as shown below (V)

wherein $R^{15}$ is a linear or branched unsaturated alkyl group having about 0 to about 20 carbon atoms, B is divalent moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; Preferably, B comprises functionalities such as alcohols, ethers, esters, amides, amines, acids and its salts, cyano, thio, urethane, urea, sulfonates, sulphonamides, phosphates and their combinations. M can be hydroxyl or halogen or epoxy or carboxylic acid group.

When $Y^2$ is an oxygen atom, the reaction products are called carbosiloxanes. Once the functionalized carbosiloxane is produced it is reacted with an alkylacryloyl compound having the general formula (VI).

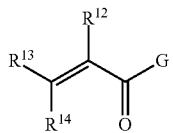
(VI)

wherein G can be a halogen or hydroxyl or alkyloxy having 1 to 10 carbon atoms. $R^{12}$ to $R^{14}$ can be selected from hydrogen or a substituted or unsubstituted saturated monovalent hydrocarbon group of 1 to about 20 carbons to produce said silicone monomer. The reaction of the functionalized carbosiloxane with alkylacryloyl compound having the general formula (VI) can be carried out in the presence of a tertiary amine base or basic ion-exchange resin (IER) or azeotrope-forming solvent or reactant. The azeotrope-forming solvent can be selected from hexane, heptane, toluene etc. and the reactant such as methylmethacrylate under the inert reaction conditions.

DETAILED DESCRIPTION OF THE INVENTION

In accordance with the present invention, compositions comprising mono-acrylate and methacrylate functionalized carbosiloxane monomers that are non-bulky and show improved hydrolysis resistance are provided. Carbosiloxane monomers of the present invention showed improved hydrolysis resistance under acidic and basic pH conditions in comparison to the corresponding conventional siloxane monomers. Cured compositions produced from these monomers showed better oxygen permeability, and surface wettability and lower modulus in comparison to compositions/films of the corresponding conventional siloxane monomers.

As used herein, "homopolymers" are polymers made from the same repeating monomer and "copolymers" are polymers wherein the polymer contains at least two structurally different monomers. Notations such as (meth)acrylate denote monomer with either acrylate or methacrylate functionality.

Also, as used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Compositions comprising (meth)acrylate functionalized silicone monomers/polymers of the present invention, products made from these compositions as well as their preparation are further described in the sections below.

In the present invention, the monomers disclosed have a carbosilane linkage, —Si—$(CH_2)_n$—Si—, which makes it possible to produce compositions having hydrolytically stable (hydrolysis resistance) monomers and polymers. In particular, the present invention is directed to compositions comprising linear mono-acrylate functional organo-modified carbosiloxane compounds useful as a hydrolytically stable silicone monomer. The mono-acrylate functional carbosiloxane monomers of the present invention have the general structure shown in formula (I):

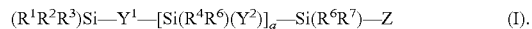
(I).

One of the preferred variants of the formula (I) of the present invention is the mono acrylate functional monomer having the general formula as shown below.

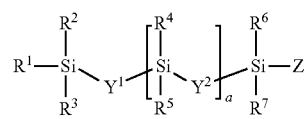

wherein a is 0 to 100; $Y^1$ is a substituted or unsubstituted divalent alkyl linking group of 1 to 10 carbon atoms, and $Y^2$ can be the same as $Y^1$ or a hetero atom such as nitrogen, oxygen or sulfur. $R^1$ to $R^7$ is independently selected from the group consisting of monovalent aliphatic, cycloaliphatic or aromatic hydrocarbon groups of 1 to about 10 carbons and halogenated hydrocarbon groups of 1 to about 10 carbons. $R^1$-$R^7$ can also be independently selected from —$Y^2$—Si($R^8R^9R^{10}$) and A, where $R^8$ to $R^{10}$ is independently selected from the group consisting of monovalent aliphatic, cycloaliphatic or aromatic hydrocarbon groups of 1 to about 10 carbons and halogenated hydrocarbon groups of 1 to about 10 carbons. A can be a monovalent hydrophilic or hydrophobic moiety selected from the group consisting of, substituted or unsubstituted, saturated and unsaturated aliphatic, cycloaliphatic or aromatic hydrocarbons and optionally contains hetero atoms. Preferably, A comprises functionalities such as alkyl, alcohol, ether, ester, amide, amine, acid and its salts, cyano, thio, urethane, urea, sulfonate, sulphonamide, phosphate and their combinations.

Z in the above structure can have the general formula (II) shown below

(II)

wherein $R^{11}$ is a linear or branched, divalent alkyl linking group having about 0 to about 20 carbon atoms.

B in general formula (II) is a divalent moiety selected from the group consisting of, substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; Preferably, B comprises functionalities such as alcohols, ethers, esters, amides, amines, acids and its salts, cyano, thio, urethane, urea, sulfonates, sulphonamides, phosphates and their combinations.

In particular, some of the representative functionalities for B are shown below.

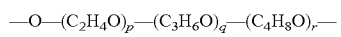

Polyether
wherein p and q are independently 0 to about 100; r is 0 to about 50 and (p+q+r) is greater than 0.

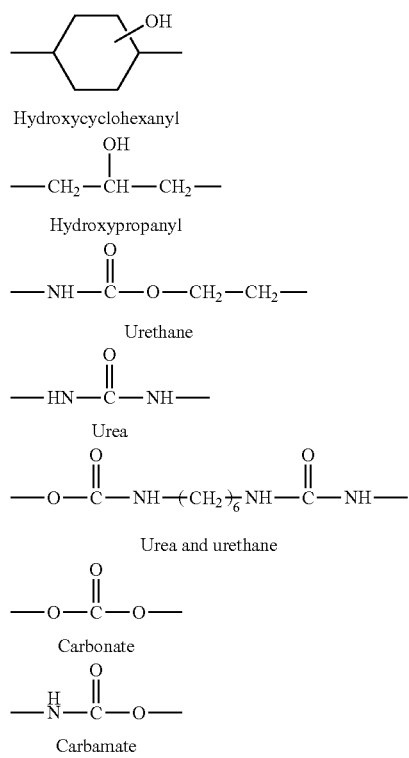

X is a polymerizable group having the general formula (III)

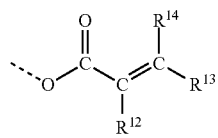

wherein $R^{12}$ to $R^{14}$ can be selected from hydrogen or a substituted or unsubstituted saturated monovalent hydrocarbon group of 1 to about 20 carbons.

The present invention is also directed to compositions comprising polymers formed by the reaction products of the carbosiloxane monomers provided herein. These polymers may be homopolymers of one of the monomers of the present invention or copolymers of two structurally different silicone monomers of the present invention, and/or copolymers of one or more silicone monomers of the present invention and at least one other hydrophilic unsaturated organic monomers suitable for use in silicone hydrogels, with preferred non-limiting examples of such being N,N-dimethylacrylamide, 2-hydroxy-ethylmethacrylate (HEMA), 2-hydroxy ethylacrylate (HEA), N-vinylpyrrolidone, and methacrylic acid. In such copolymers, the ratio of the silicone monomers of the present invention to the other hydrophilic unsaturated organic monomers is from about 1:100 to about 100:1 and preferably from about 20:80 to about 90:10 and more preferably from about 30:70 to about 80:20.

The unsaturated organic monomers and the carbosiloxane monomers of this invention are mutually miscible and form homogeneous mixtures. The use of compatibilizing solvents is not necessary. The carbosiloxane monomers of this invention are also either water-soluble or water-dispersible. Water-soluble carbosiloxane monomers are miscible with water in all proportions to yield homogeneous solutions. Water-dispersible carbosiloxane monomers do not dissolve completely in water. Cloudiness, haze, colloid formation and similar visible signs of heterogeneity in the aqueous mixture are indicative of dispersion rather than solution. Both water solubility and water dispersibility are desirable features of the carbosiloxane monomers of the instant invention. When the carbosiloxane monomers contain a methacrylated ethoxylated polyether segment, water dispersibility is observed when the polyether content is less than about 60 weight percent of the total molecular weight, and water solubility when the polyether segment is greater than about 60 weight percent.

Prior to forming compositions comprising polymers, the polymers are formed by mixing the desired monomers and the resulting mixture is polymerized and cured to form transparent thin films by known thermal techniques using free radical or cationic or anionic initiators and UV cure techniques using photoinitiators in the presence of cross-linking agents. The monomers added to the reaction mixture to form the polymers may be monomers or prepolymers. A "prepolymer" is a reaction intermediate polymer of medium molecular weight having polymerizable groups. Thus, it is understood that the terms "silicone-containing monomers", "carbosiloxane monomers" and "hydrophilic monomers" include prepolymers.

One preferred variant of carbosiloxane monomer from structure (I) of the present invention has the following formula

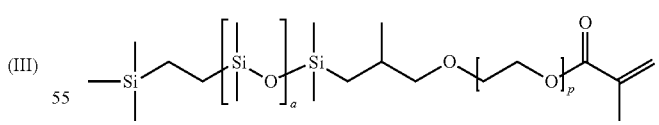

wherein B is a divalent polyether as shown in the representative example with p being 0 to about 100, preferably 2 to about 15, more preferably about 8, and q and r equal to 0; $Y^1$ is a divalent alkyl-linking group of about 1 to 10 carbons, preferably 1 to about 5 carbons, more preferably about 2 carbons. $Y^2$ is a combination of divalent heteroatom and divalent alkyl group and X is polymerizable methacrylate group, a is 0 to about 100, more preferably 0 to 20 inclusive, and even more preferably 1. Each of the R groups in the general monomer structure (I) is a monovalent alkyl-linking group, preferably a methyl group. $R^1$ to $R^7$ can also be selected from $-Y^2-Si(R^8R^9R^{10})$ and A.

Another preferred variant of carbosiloxane monomer from structure (I) of the present invention has the following formula

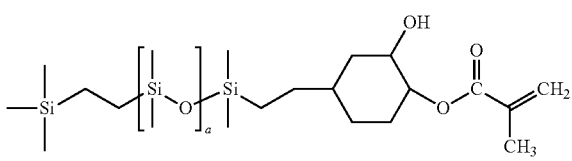

wherein B is a divalent hydroxyl containing cycloaliphatic ring; X is polymerizable methacrylate group, a is 0 to about 100, more preferably 0 to about 20 inclusive, and even more preferably 1. $Y^1$ is a divalent alkyl-linking group of about 1 to 10 carbons, preferably 1 to about 5 carbons, more preferably about 2 carbons. $Y^2$ is a combination of divalent heteroatom and divalent alkyl group. Each of the R groups in the general monomer structure (I) is a monovalent alkyl-linking group, preferably a methyl group. $R^1$ to $R^7$ can also be selected from $-Y^2-Si(R^8R^9R^{10})$ and A.

Yet another preferred variant of carbosiloxane monomer from structure (I) of the present invention has the following formula

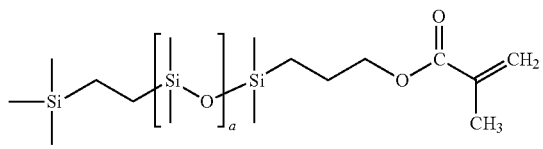

wherein B is a divalent alkyl group; X is polymerizable methacrylate group, a is 0 to about 100, more preferably 0 to about 20 inclusive, and even more preferably 1. $Y^1$ is a divalent alkyl-linking group of about 1 to about 10 carbons, preferably 1 to about 5 carbons, more preferably about 2 carbons. $Y^2$ is a combination of divalent heteroatom and divalent alkyl group. Each of the R groups in the general monomer structure (I) is a monovalent alkyl-linking group, preferably a methyl group. $R^1$ to $R^7$ can also be selected from $-Y^2-Si(R^8R^9R^{10})$ and A.

Another embodiment of the present invention is directed to a process for producing the described carbosiloxane monomers comprising chemically reacting a carbosiloxane compound with SiH functionality having the general formula shown below $$(R^1R^2R^3)Si-Y^1-[Si(R^4R^5)(Y^2)]_a-Si(R^6R^7)-H \quad (IV)$$

wherein a is 0 to 100; $Y^1$ is a substituted or unsubstituted divalent alkyl linking group of 1 to 10 carbon atoms, and $Y^2$ can be $Y^1$ or a divalent hetero atom. $R^1$ to $R^7$ is independently selected from the group consisting of monovalent aliphatic, cycloaliphatic or aromatic hydrocarbon groups of 1 to about 10 carbons and halogenated hydrocarbon groups of 1 to about 10 carbons. Also, $R^1$-$R^7$ can be $-Y^2-Si(R^8R^9R^{10})$ and A, wherein $R^8$ to $R^{10}$ is independently selected from the group consisting of monovalent aliphatic, cycloaliphatic or aromatic hydrocarbon groups of 1 to about 10 carbons and halogenated hydrocarbon groups of 1 to about 10 carbons. A can be a monovalent hydrophilic or hydrophobic moiety selected from the group consisting of, substituted or unsubstituted, saturated and unsaturated aliphatic, cycloaliphatic or aromatic hydrocarbons and optionally contains hetero atoms. Once produced, a compound of general formula (IV) is reacted with a terminally unsaturated compound having the general formula as shown below (V)

wherein $R^{15}$ is a linear or branched unsaturated alkyl group having about 0 to about 20 carbon atoms, B is divalent moiety selected from the group consisting of substituted or unsubstituted, saturated and unsaturated aliphatic, cycloaliphatic or aromatic hydrocarbons and substituted or unsubstituted, saturated and unsaturated aliphatic, cycloaliphatic or aromatic hydrocarbons containing hetero atoms; Preferably, B comprises functionalities such as alcohols, ethers, esters, amides, amines, acids and its salts, cyano, thio, urethane, urea, sulfonates, sulphonamides, phosphates and their combinations. M can be hydroxyl or halogen or epoxy or carboxylic acid group.

Once the functionalized carbosiloxane is produced, it is reacted with an alkylacryloyl compound having the general formula (VI).

wherein G can be a halogen or hydroxyl or alkyloxy having 1 to 10 carbon atoms. $R^{12}$ to $R^{14}$ can be selected from hydrogen or a substituted or unsubstituted saturated monovalent hydrocarbon group of 1 to about 20 carbons to produce said silicone monomer. The reaction of the functionalized carbosiloxane with alkylacryloyl compound having the general formula (VI) can be carried out in the presence of a tertiary amine base or basic ion-exchange resin (IER) or azeotrope forming solvent or reactant. The azeotrope forming solvent can be selected from hexane, heptane, toluene etc. and the reactant such as methylmethacrylate under the inert reaction conditions.

Once the monomers and polymers are produced as discussed above, they can be mixed with other monomers or polymers that are the same or different to produce the compositions of the present invention. These compositions have been found to have properties that are favorable for use in the cosmetic and medical industries. Some examples and discussions of the different uses for the compositions are provided herein below.

Uses for the Compositions of the Present Invention:

I. Health Care:

The silicone hydrogel copolymers are gaining importance in the health care industry for various applications such as contact lens, wound management and drug delivery applications because of their improved oxygen permeability compared to conventional hydrogels. One of the key challenges in health care is that the material used for these applications should be dimensionally and chemically stable and should not undergo hydrolytic degradation and leach out degradation products under the conditions of use, such as sterilization, storage in aqueous media containing buffers, etc. The carbosiloxane monomer of the instant invention shows improved hydrolytic stability over the conventional siloxane monomer, which enables it to produce silicone hydrogel copolymers with improved hydrolytic stability for health-care related applications, further details of which are shown in the following paragraphs. Also, its mono-functional polymerizable group (mono-acrylate or mono-methacrylate functionality) affords better control to produce silicone hydrogel copolymers with desired modulus depending upon the end applications.

A. Contact Lens:

The advantages of using the mono-functional carbosiloxane monomer of the instant invention for contact lens application are numerous. For example, (1) the presence of carbosiloxane linkage, —Si—$(CH_2)_n$—Si—, in the siloxane monomer composition of the present invention can help to produce soft hydrogel contact lens materials with improved hydrolytic stability. That means the silicone hydrogel contact lenses produced are hydrolytically stable and will not change in their chemical composition and physical dimensions when they are subjected to usage conditions, for e.g., in the eye or in the disinfecting solution or during sterilization. The contact lens material of the instant invention is also resilient. When the term resilient is used herein it is meant that after the lenses have been deformed the lenses will return quickly to their original shape. (2) The monomers of the instant invention, containing hydrophilic side chains, are compatible with hydrogel co-monomers in the entire range of compositions without employing any solvent or compatibilizing agents. The copolymer films obtained with various hydrogel comonomers and the mixtures thereof are transparent, water absorbing with inherently wettable surface. (3) Furthermore, the human cornea requires about $2 \times 10^{-6}$ $cm^3$/(sec. $cm^2$ atm.) of oxygen through the contact lens for better eye health as reported by Hill and Fatt (American Journal of Optometry and Archives of the American Academy of Optometry, Vol. 47, p. 50, 1970). The silicone-hydrogel contact lens materials made from the monomer of the instant invention allows better transmission of oxygen through itself to supply the necessary oxygen requirements of the human cornea. (4) The monomer of the instant invention can be used to produce hydrogel copolymer with the desired lower modulus to improve the comfort of the lens wearers. (5) The contact lens material can be produced with the monomer of the present instant invention employing the cure techniques (for eg. thermal and actinic radiation cure methods) known in the art with out employing solvent or compatibilizing agents.

B. Wound Management Devices:

Hydrogels with high water content and oxygen permeability are needed to produce the wound-management devices (for eg. transdermal patches, wound healing patches, wound dressing patches etc). The water present in the wound-dressing material helps to provide a moist environment for better comfort and painless wound management. Oxygen also plays an important role in wound healing and the lack of oxygen transport in the wound dressing material has been identified as one of the most common issues affecting the wound healing process (Bok Y. Lee "The Wound Management Manual", McGraw-Hill, New York, 2005, p. 44). Oxygen transport to the wound through hemoglobin is an important process for wound healing. However, the damaged tissue in the wound can act as a barrier to hemoglobin leading to localized hypoxia at the wound site. Damaged tissue is generally hypoxic due to the large consumption of oxygen by cells. Leukocytes consume oxygen to produce infection-fighting oxidants. In addition, fibroblasts and endothelial cells also require oxygen for wound healing. Therefore, the only way of oxygen transport to the exterior part of the wound is from the atmosphere and this requires the wound dressing to have good oxygen permeability for better healing of the wounds. The monomer of the instant invention having hydrophilic moieties such as polyethers or other hydrophilic moieties can provide silicone hydrogels that are not only hydrolytically stable, but also water absorbing and highly oxygen permeable making them a suitable wound dressing material for various wound management applications. Hydrophilic silicone compositions of the present invention can also provide an excellent moist environment for better comfort and painless wound management. The silicone composition of current invention can be used as a potential carrier or device for various active ingredients and controlled release of those actives under different conditions (for example, pH, pressure, temperature, chemical reaction etc).

C. Targeted and Controlled Delivery of Bio-actives:

The ease of administration of drugs and the large surface area for absorption makes the gastro intestinal (GI) tract as the most popular route for drug delivery. Currently, several hydrogels are being investigated as potential devices for site-specific drug delivery for effective therapy. For example, biocompatible hydrogels are used as colon-specific drug delivery systems for the treatment of *helicobacter pylori* infection in peptic ulcer disease. These biocompatible hydrogels are designed to be highly swollen and to degrade in the presence of colonic enzymes or micro flora, providing colon-specific drug delivery. Additionally, biocompatible hydrogels protect insulin in the harsh, acidic environment of the stomach before releasing the drug in the small intestine. The hydrophilic silicone compositions of the present invention can be used to produce biocompatible silicone hydrogel-based drug delivery devices to release the drug locally to specific sites in the GI tract. The hydrophilic silicone compositions of this invention can also be used for other biocompatible drug delivery applications such as puncta plugs, ophtha coils, retinal implants, transdermal patches, wound healing patches, transdermal iontophoresis etc.

D. Transdermal Delivery:

The silicone compositions of the present invention can be used for the transdermal drug delivery applications. Drug delivery to the skin has been generally used to treat skin diseases or for disinfections of the skin. In recent years, transdermal route for the delivery of drugs has been investigated. Swollen soft hydrogels are explored to deliver the drugs for long period of duration and these hydrogels can be easily removed from the skin without pain and improves comfort for the patients. Current research in this field is now focused on iontophoresis and electroporation. Hydrogel-based formulations are being explored for electrically assisted delivery using transdermal iontophoresis for enhanced permeation of products such as, hormones and nicotine.

E. Subcutaneous Delivery:

The silicone compositions of the present invention can be used for the subcutaneous drug delivery applications also. Among the various possible therapeutic applications of hydrogels, the most substantial application is implantable therapeutic devices. Hydrogel formulations having high water content, environmentally similar to biological tissue, make them relatively biocompatible and proposed for subcutaneous delivery of drugs. For example, hydrogels can be used for delivery of proteins and peptides. Currently, implantable hydrogels are leading towards the development of biodegradable systems, which do not require surgical removal of the drug-loaded implants.

Other health care applications include scaffolds for tissue engineering, anti-microbial devices, anti-bacterial devices, antifouling coatings, and anti-fungal devices.

II. Pesticides—Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhanced spreading to improve spray coverage, or to provide penetration of the herbicide into the plant cuticle. These adjuvants are provided either as a tank-side additive or used as a component in pesticide formulations. Typical uses for pesticides include agricultural, horticultural, turf, ornamental, home and garden, veterinary and forestry applications.

The silicone compositions of the present invention and its polymer can be used as a hydrolytically stable surfactant in pesticidal compositions at an amount sufficient to deliver between 0.005% and 2% to the final use concentration, either as a concentrate or diluted in a tank mix. Optionally the pesticidal composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, Bacillus thuringiensis, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

Fertilizers and micronutrients include, but not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, calcium chloride, The pesticide or fertilizer may be a liquid or a solid. If a solid, it is preferable that it is soluble in a solvent, or the organomodified siloxanes of the present invention, prior to application, and the silicone may act as a solvent, or surfactant for such solubility or additional surfactants may perform this function.

III. Coatings:

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exist as, foul-resistant coatings, biological coatings, seed coatings, solvent-borne coatings, water-borne coatings and powder coatings.

The coatings components may be employed as: architecture coatings; OEM product coatings such as automotive coatings and coil coatings; Special Purpose coatings such as industrial maintenance coatings and marine coatings;

Typical resin types include: Polyesters, alkyds, acrylics, epoxies and combinations thereof.

V. Personal Care:

The organomodified siloxane compositions of the present invention may be utilized in personal care emulsions, such as lotions, and creams. As is generally known, emulsions comprise at least two immiscible phases one of which is continuous and the other is discontinuous. Furthermore, emulsions may be liquids with varying viscosities or solids. Additionally, the particle size of the emulsions may render them microemulsions or miniemulsions and, when the particle sizes are sufficiently small, these emulsions may be transparent. Further, it is also possible to prepare emulsions of emulsions and these are generally known as multiple emulsions. These emulsions may be: 1) Aqueous emulsions, where the discontinuous phase comprises water and the continuous phase comprises the organomodified siloxane composition of the present invention. 2) Aqueous emulsions, where the discontinuous phase comprises the organomodified siloxane composition of the present invention and the continuous phase comprises water. 3) Non-aqueous emulsions, where the discontinuous phase comprises a non-aqueous hydroxylic solvent and the continuous phase comprises the organomodified siloxane composition of the present invention and 4) Non-aqueous emulsions, where the continuous phase comprises a non-aqueous hydroxylic organic solvent and the discontinuous phase comprises the organomodified siloxane composition of the present invention.

The monomer of the instant invention can be polymerized using emulsion polymerization and the copolymer of these monomer obtained with acrylic comonomers forms excellent films which can be used for various skin care and hair care applications (for eg, mascara, styling gels, sun protection films etc). Suitable personal care compositions are made by combining, in a manner known in the art, for example, by mixing one or more of the above components with the organomodified siloxane composition of the present invention. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

VI. Home Care:

The organomodified siloxane composition of the present invention and its polymers can be used as surfactants in home care applications, such as, laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

SYNTHETIC EXAMPLES

The following examples are illustrative only and should not be construed as limiting the invention, which is properly delineated in the appended claims. Mono-methacrylated carbosiloxane monomers having different functionality were produced as shown below.

Monomer Preparation

Example 1

Synthesis of Compound Represented by the Formula

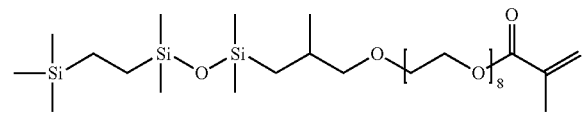

This monomer was prepared using two-step process. In the first step, a hydrosilylation reaction occurs between hydroxyl terminated methallyl polyether and mono-hydride functional carbosiloxane. In the second step, the hydroxyl group is converted into polymerizable methacrylate group through a methacrylation reaction. The mono-hydride functional carbosiloxane was prepared using the process disclosed in U.S. Pat. No. 7,259,220 B1, which is herein incorporated in its entirety by reference.

In a specific process, 1-(2-trimethylsilylethyl)-1,1,3,3-tetramethyldisiloxane (25 g), a hydride functional carbosiloxane, and a methallyl-terminated polyethylene glycol (46 g), having an average of 8 ethylene oxide (EO) units in the chain, were introduced into 250 mL three-neck round bottom (RB) flask equipped with a reflux condenser, mechanical stirrer, temperature controller with thermocouple and a nitrogen inlet. The contents were heated to 80° C. to 90° C. in presence of Karstedt's catalyst (50 to 100 ppm of Pt with respect to total reactant charge) and buffer (U.S. Pat. No. 5,986,122) to prevent side reactions like dehydrocoupling reaction from taking place. After completion of the hydrosilylation, volatile compounds were removed from the reaction product under reduced pressure. The final product, hydroxyl terminated carbosiloxane polyether, was obtained as a colorless, transparent liquid in quantitative yield without any undesired side products. The resultant pure product was well characterized by multinuclear NMR spectroscopy. Synthesis of the silicone polyethers of the present invention can occur with or without solvent. If solvents are used, preferred ones include toluene, isopropyl alcohol or methyl ethyl ketone.

H-NMR (ppm): 0.02 (Si(CH$_3$), 0.3 & 0.6 (SiCH$_2$CH), 0.4 (SiCH$_2$CH$_2$Si), 1.0 (Si(CH$_3$), 1.9 (—CH<), 3.2 & 3.3 (>CH—CH$_2$—O—), 3.6 (—CH$_2$CH$_2$O—).

Si—NMR (ppm): 3.4 (Si(CH$_3$)$_3$CH$_2$), 7.2 (O—Si(CH$_3$)$_2$(CH$_2$)), 8.5 (O—Si(CH$_3$)$_2$(CH$_2$CH$_2$).

Next, the carbosiloxane polyether that was synthesized in the step above, triethylamine (11.3 g) and methylethylketone (100 ml) were introduced into three-neck one liter RB flask equipped with dropping funnel and a stirring blade. The flask was immersed in an ice bath and methacryloyl chloride (11.2 g) was added drop wise using dropping funnel over a period of approximately 1 hour with constant stirring. After completion of the addition the stirring was continued for another 3 hours at room temperature. The triethylamine hydrochloride salt that precipitated out during the reaction was filtered off. The solvent was removed with a rotary vacuum evaporator and the final monomer was obtained as colorless to pale yellow, transparent liquid. The low boiling point of the solvent used enables the solvent to be removed completely at a temperature of about 30° C. to 40° C. under vacuum (i.e. less than about 10 mm Hg). The resulting monomer was well characterized by infrared spectroscopy, multinuclear NMR spectroscopy.

H-NMR (ppm): 0.02 (Si(CH$_3$), 0.3 & 0.6 (SiCH$_2$CH), 0.4 (SiCH$_2$CH$_2$Si), 0.98 (Si(CH$_3$), 1.98 (CH$_3$), 3.1 & 3.3 (>CH—CH$_2$—O—), 3.64 (—CH$_2$CH$_2$O—), 4.2 (CH$_2$COO), 5.6 & 6.15 (CH$_2$=).

Si—NMR (ppm): 3.5 (Si(CH$_3$)$_3$CH$_2$), 7.2 (O—Si(CH$_3$)$_2$(CH$_2$)), 8.4 (O—Si(CH$_3$)$_2$(CH$_2$CH$_2$).

Example 2

Synthesis of Compound Represented by the Formula

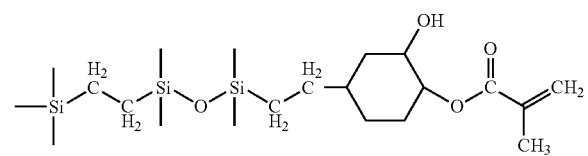

This monomer was prepared was also prepared using two-step process. In the first step, a hydrosilylation reaction occurs between hydride functional carbosiloxane and vinyl functional cyclohexene epoxide. In the second step, the epoxide group is reacted with unsaturated acids to introduce polymerizable group in it.

In a specific process, 1-(2-trimethylsilylethyl)-1,1,3,3-tetramethyldisiloxane (25 g) and vinyl cyclohexene epoxide (13.2 g) were introduced into 250 mL three-neck round bottom (RB) flask equipped with a reflux condenser, mechanical stirrer, temperature controller with thermocouple and a nitrogen inlet. The contents were heated to 80° C. to 90° C. in presence of Karstedt's catalyst (10 to 50 ppm Pt with respect to total reactant charge) and buffer (U.S. Pat. No. 5,986,122) to prevent side reactions like dehydrocoupling reaction from taking place. After completion of the hydrosilylation, distilling out unwanted volatile compounds under reduced pressure purified the reaction product. The final product, epoxy functional carbosiloxane, was obtained as colorless, transparent liquid in quantitative yield without any undesired side products. The resultant pure product was well characterized by proton NMR spectroscopy. The epoxy functional carbosiloxane of the present invention can occur with or without solvent. If solvents are used, preferred ones include toluene, isopropylalcohol or methyl ethyl ketone.

H-NMR (ppm): 0.02 (Si(CH$_3$), 0.4 (SiCH$_2$CH$_2$Si), 0.5 (SiCH$_2$), 1.2 to 2 (CH$_2$).

Next, the epoxy functional carbosiloxane synthesized above, titanium isopropoxide (0.4 wt % with respect to carbosiloxane) and hydroquinone (0.0025 wt % with respect to carbosiloxane) were introduced into three-neck one liter RB flask equipped with dropping funnel and a stirring blade. The flask was heated to 90 deg C. in an oil bath and then acrylic acid (7.68 g) was added in a drop wise manner into the RB with constant stirring. After completion of the addition the stirring was continued for another 5 hours at 90 deg C. The solvent (toluene) and other volatile impurities were removed with a rotary vacuum evaporator and the final monomer was obtained as colorless, transparent liquid. The resulting mono-acrylated carbosiloxane monomer was well characterized by infrared spectroscopy, proton NMR spectroscopy.

H-NMR (ppm): 0.02 (Si(CH$_3$), 0.4 (SiCH$_2$CH$_2$Si), 0.5 (SiCH$_2$), 1.2 to 2 (CH$_2$), 3.8 & 4.8 (CH$_2$), 5.8, 6.2 & 6.4 (CH$_2$=CH—).

Example 3

Formation of Silicone-Hydrogel Films

The compound obtained in Example 1 (49 parts by weight), 2-hydroxy ethyl methacrylate (49 parts by weight), ethylene glycol dimethacrylate (EGDMA) (1 part by weight), and benzoyl peroxide (1 part by weight) were mixed and stirred. The resulting clear, homogeneous and transparent reaction mixture was purged with nitrogen gas and poured into a stainless steel mould. The thin film of the reaction mixture was thermally cured at 85° C. for 8 hours using hot air oven. The silicone hydrogel film thus produced was transparent and water absorbing.

Example 4

A silicone-hydrogel film was obtained in the same way as in Example 3 except that the compound obtained in Example 2 was used instead of compound obtained in Example 1. The silicone hydrogel film thus produced was transparent and water absorbing.

Comparative Example 1 (CEx. 1)

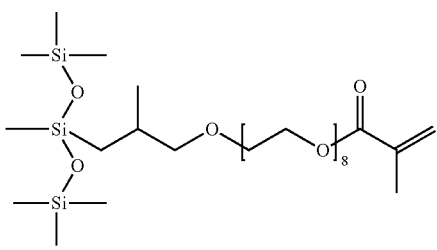

The monomer was prepared in the same way as in Example 1 except that 1,1,1,3,5,5,5-heptamethyltrisiloxane was used instead of 1-(2-trimethylsilylethyl)-1,1,3,3-tetramethyldisiloxane. The mono-acrylated siloxane monomer produced was well characterized by infrared spectroscopy, multinuclear NMR spectroscopy.

H-NMR (ppm): 0.02 (Si(CH$_3$), 0.3 & 0.6 (SiCH$_2$CH), 0.98 (Si(CH$_3$), 1.98 (CH$_3$), 3.1 & 3.3 (>CH—CH$_2$—O—), 3.64 (—CH$_2$CH$_2$O—), 4.3 (CH$_2$COO), 5.6 & 6.15 (CH$_2$=).

Si—NMR (ppm): 8 (—Si(CH$_3$)$_3$), −22 (O—Si(CH$_3$)$_2$—).

Hydrolytic stability of the monomer of the present invention was measured using HPLC (US Pub. Pat Appl. 20100069279). 0.5 wt % of the monomers obtained in Example 1 (Ex.1) is introduced into three different vials containing 6.5, 7 and 7.5 pH solutions. The vials were sealed with leak proof seal and heated to 85 deg C. The heat accelerated hydrolytic degradation composition changes were monitored using HPLC as a function of time. The monomer of the current invention (Ex.1) showed improved hydrolytic stability under acidic, basic and neutral conditions in comparison to the conventional siloxane monomer (CEx.1) over the acidic, neutral and basic pH conditions.

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A silicone composition comprising of at least one carbosiloxane linkage having the following formula

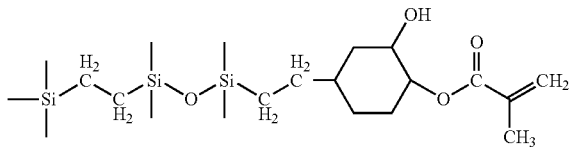 [SMILES: C=C(C)C(=O)OC1CCC(CC[Si](C)(C)O[Si](C)(C)CC[Si](C)(C)C)CC1O]

wherein the silicone composition has improved hydrolytic stability.

2. A health care composition comprising the silicone composition of claim 1 wherein the health care formulation comprises bioactives, anti-acne agents, anti-ageing agents, anti-caries agents, anti-fungal agents, anti-microbial agents, anti-oxidants, anti-cancer, anti-viral, anti-inflammatory, anti-coagulants, hemostatic agents, exfoliants, hormones, enzymes, medicinal compounds, biocides, external analgesics, oral care agents, oral care drugs, oxidizing agents, reducing agents, skin protectants, essential oils, insect repellents, UV light absorbing agents, solar filters, pigments, hydrating agents, vitamins and their combinations thereof.

3. The health care composition of claim 2 comprising the silicone composition of claim 1, which can be used for health care application further comprising hydrogels, drug delivery systems, transdermal patches, wound healing patches, wound dressing patches, puncta plugs, ophtha coils, retinal implants, transdermal iontophoresis, scaffold for tissue engineering, anti-microbial devices, anti-bacterial devices, biofilm resistant coatings, anti-fungal devices, wound management devices, ophthalmic devices, bioinserts, prostheses and body implants.

4. A personal care composition comprising the silicone composition of claim 1, wherein the personal care formulation comprises surfactants, emulsifiers, solvents, emollients, emollients, moisturizers, humectants, pigments, colorants, fragrances, biocides, preservatives, chelating agents, antioxidants, anti-microbial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, thickening agents, particulate fillers, silicones, clays, plasticizers, occlusives, sensory enhancers, esters, resins, film formers, film forming emulsifiers, high refractive index materials and their combinations thereof.

5. The personal care composition of claim 4 comprising the silicone composition of claim 1, which can be used for personal care application further comprising antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouthwashes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail-and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprises at least one of the foregoing applications.

6. A pesticide formulation comprises the silicone composition of claim 1.

7. A fertilizer formulation comprises the silicone composition of claim 1.

8. A fertilizer coating, seed coating, anti-fouling coating, waterborne coating formulation comprising of the silicone composition of claim 1.

9. A process of making the silicone composition of claim 1 comprises reacting:
1-(2-trimethylsilylethyl)-1,1,3,3-tetnunethvldisiloxane;
with terminally unsaturated vinyl cyclohexene epoxide
to produce an epoxy functionalized carbosiloxane
and reacting the epoxy functionalized carbosiloxane with acrylic acid
to produce said silicone monomer having the formula of claim 1.

10. The process of claim 9, wherein said reaction of said functionalized carbosiloxane with said alkylacryloyl compound is carried out in the presence of at least one tertiary base or at least one ionic exchange resin (IER) and a low boiling polar solvent, the process of claim 9 wherein the amount of carbosiloxane reacted is present in an amount that ranges from about 5 to about 90 weight percent of the total composition, and the amount of alkyacryloyl is present in an amount that ranges from about 5 to about 80 weight percent of the total composition.

11. A health care composition comprising the silicone composition prepared from the process of claim 9, wherein the health care formulation comprises bioactives, anti-acne agents, anti-ageing agents, anti-caries agents, anti-fungal agents, anti-microbial agents, anti-oxidants, anti-cancer, anti-viral, anti-inflammatory, anti-coagulants, hemostatic agents, exfoliants, hormones, enzymes, medicinal compounds, biocides, external analgesics, oral care agents, oral care drugs, oxidizing agents, reducing agents, skin protectants, essential oils, insect repellents, UV light absorbing agents, solar filters, pigments, hydrating agents, vitamins and their combinations thereof.

12. The health care composition of claim 11 comprising the silicone composition prepared from the process of claim 9, which can be used for health care application further comprising hydrogels, drug delivery systems, transdermal patches, wound healing patches, wound dressing patches, puncta plugs, ophtha coils, retinal implants, transdermal iontophoresis, scaffold for tissue engineering, anti-microbial devices, anti-bacterial devices, biofilm resistant coatings, anti-fungal devices, wound management devices, ophthalmic devices, bioinserts, prostheses and body implants.

13. A personal care composition comprising the silicone composition prepared from the process of claim 9, wherein the personal care formulation comprises surfactants, emulsifiers, solvents, emollients, moisturizers, humectants, pigments, colorants, fragrances, biocides, preservatives, chelating agents, antioxidants, anti-microbial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, thickening agents, particulate fillers, silicones, clays, plasticizers, occlusives, sensory enhancers, esters, resins, film formers, film forming emulsifiers, high refractive index materials and their combinations thereof.

14. The personal care composition of claim 13 comprising the silicone composition prepared from the process of claim 9, which can be used for personal care application further comprising comprises antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-fizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail-and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprises at least one of the foregoing applications.

15. A pesticide formulation comprises the silicone composition prepared from the process of claim 9.

16. A fertilizer formulation comprises the silicone composition prepared from the process of claim 9.

17. A fertilizer coating, seed coating, anti-fouling coating, waterborne coating formulation comprising the silicone composition prepared from the process of claim 9.

\* \* \* \* \*